(12) United States Patent
Endoh et al.

(10) Patent No.: US 8,190,239 B2
(45) Date of Patent: May 29, 2012

(54) INDIVIDUAL IDENTIFICATION DEVICE

(75) Inventors: Toshio Endoh, Kawasaki (JP); Takahiro Aoki, Kawasaki (JP); Makoto Goto, Kawasaki (JP); Masaki Watanabe, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 348 days.

(21) Appl. No.: 11/046,698

(22) Filed: Feb. 1, 2005

(65) Prior Publication Data
US 2005/0148876 A1    Jul. 7, 2005

Related U.S. Application Data

(63) Continuation of application No. PCT/JP02/08944, filed on Sep. 3, 2002.

(51) Int. Cl.
*A61B 6/00* (2006.01)
(52) U.S. Cl. .................. 600/473; 600/475; 382/115
(58) Field of Classification Search .................. 600/310, 600/473, 407, 475, 479; 356/51; 250/334, 250/339.11, 339.14; 382/115, 125
See application file for complete search history.

(56) References Cited

U.S. PATENT DOCUMENTS

| | | | | |
|---|---|---|---|---|
| 3,648,240 A | * | 3/1972 | Jacoby et al. | 382/115 |
| 4,393,366 A | * | 7/1983 | Hill | 382/117 |
| 4,699,149 A | * | 10/1987 | Rice | 600/475 |
| 5,007,428 A | * | 4/1991 | Watmough | 600/440 |
| 5,793,881 A | | 8/1998 | Stiver et al. | |
| 6,173,068 B1 | * | 1/2001 | Prokoski | 382/115 |
| 6,301,375 B1 | * | 10/2001 | Choi | 382/115 |
| 6,330,346 B1 | | 12/2001 | Peterson et al. | |
| 6,529,814 B2 | * | 3/2003 | Ishizu et al. | 701/96 |
| 6,616,613 B1 | * | 9/2003 | Goodman | 600/504 |
| 6,993,160 B2 | * | 1/2006 | Miura et al. | 382/115 |
| 2001/0006493 A1 | * | 7/2001 | Ikeda et al. | 369/13 |
| 2002/0028004 A1 | | 3/2002 | Miura et al. | |
| 2002/0048014 A1 | | 4/2002 | Kono et al. | |
| 2004/0001617 A1 | * | 1/2004 | Blume | 382/126 |

FOREIGN PATENT DOCUMENTS

| | | |
|---|---|---|
| GB | 2 156 127 | 10/1985 |
| JP | 1-503203 | 11/1989 |
| JP | 10-127609 | 5/1998 |
| JP | 10-295674 | 11/1998 |

(Continued)

OTHER PUBLICATIONS

Notice of Rejection Grounds for corresponding Japanese Application No. 2004-534066 dated Feb. 21, 2006.

*Primary Examiner* — Ruth S Smith
(74) *Attorney, Agent, or Firm* — Staas & Halsey LLP

(57) ABSTRACT

In order to provide an individual identification device for enabling good blood-vessel imaging even in a noncontact way and using an identifying method suitable for noncontact imaging, the device comprises an imaging device for imaging blood vessels of a hand of the user in a noncontact way including a position/direction/shape instructing unit for instructing the user to hold up his hand, one or more irradiating units for irradiating the hand with near infrared radiation, and one or more imaging units for producing an image by near infrared radiation; a blood-vessel image extracting unit for extracting the blood-vessel image from the produced image; a blood-vessel image storage unit for storing the hand blood-vessel image of each user; and an identifying unit for identifying the user by comparing the extracted blood-vessel image with the registered blood-vessel image.

23 Claims, 20 Drawing Sheets

| | FOREIGN PATENT DOCUMENTS | |
|---|---|---|
| JP | 11-203452 | 7/1999 |
| JP | 11-512203 | 10/1999 |
| JP | 2000-5148 | 1/2000 |
| JP | 2000-259817 | 9/2000 |
| JP | 2001-215109 | 8/2001 |
| JP | 2001-273497 | 10/2001 |
| JP | 2002-015297 | 1/2002 |
| JP | 2002-083298 | 3/2002 |
| JP | 2002-92616 | 3/2002 |
| JP | 2002-133417 | 5/2002 |
| JP | 2003-187235 | 7/2003 |
| WO | WO88/04153 | 6/1988 |
| WO | WO 88/04153 * | 6/1988 |

* cited by examiner

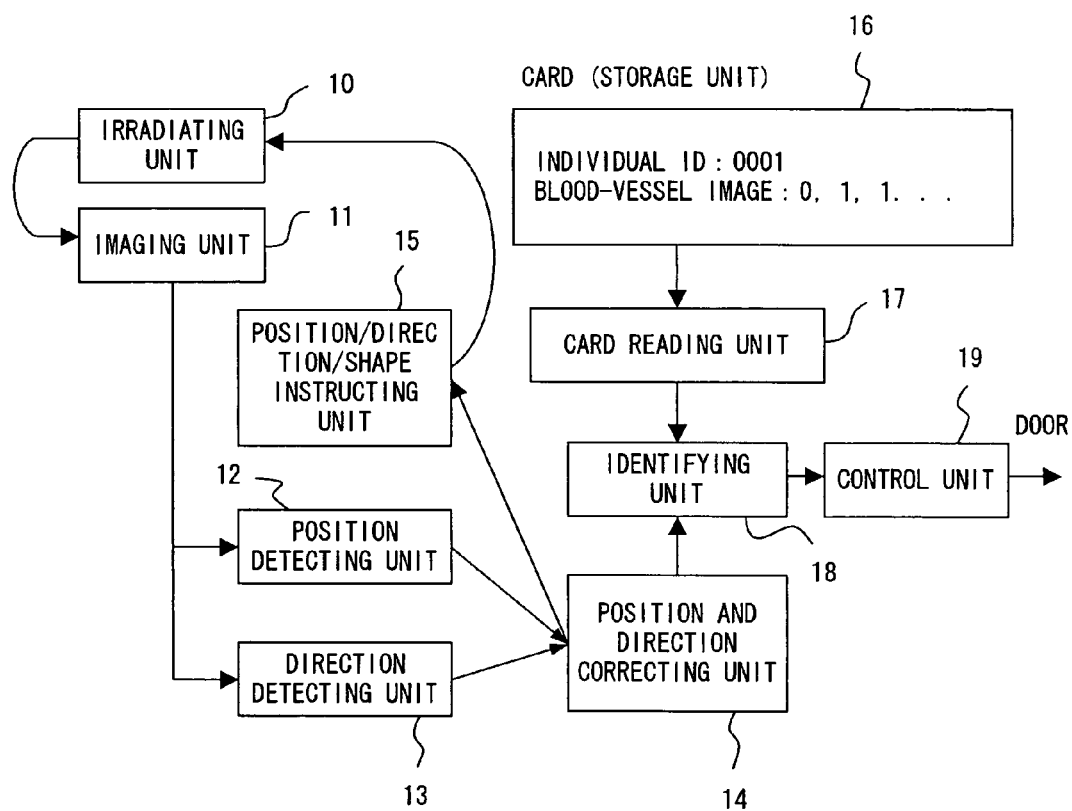
F I G. 2

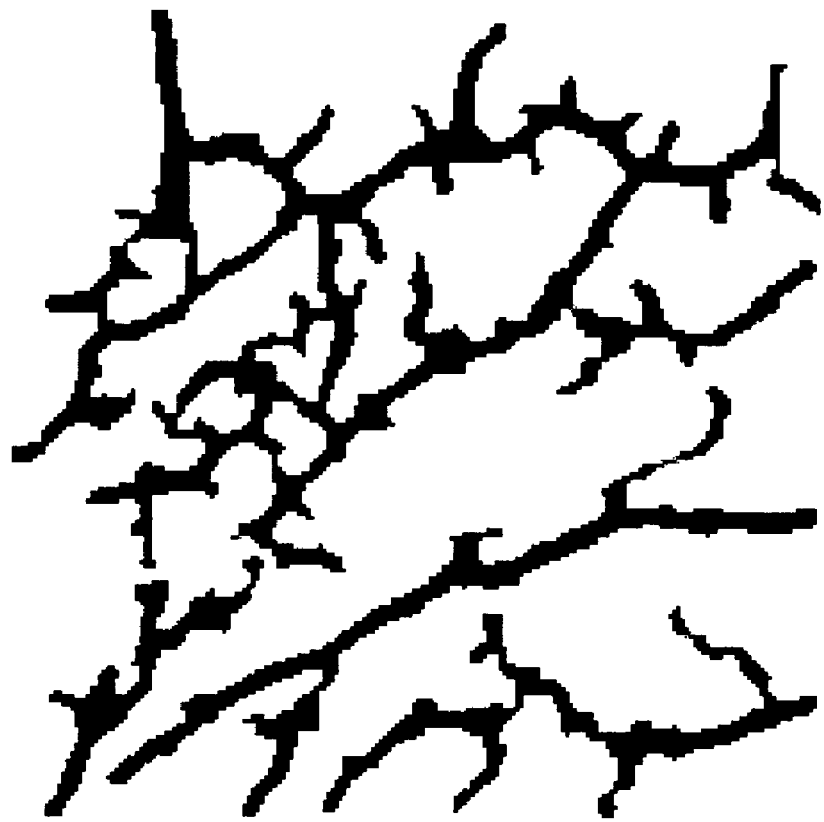
F I G. 5

| INDIVIDUAL ID | BLOOD-VESSEL IMAGE |
| --- | --- |
| 0001 | 0, 0, 0, 1, 1, 1, 0, 0, 0, ⋯ |
| 0002 | 0, 0, 0, 1, 1, 1, 0, 0, 0, ⋯ |
| ⋮ | ⋮ |

F I G. 6

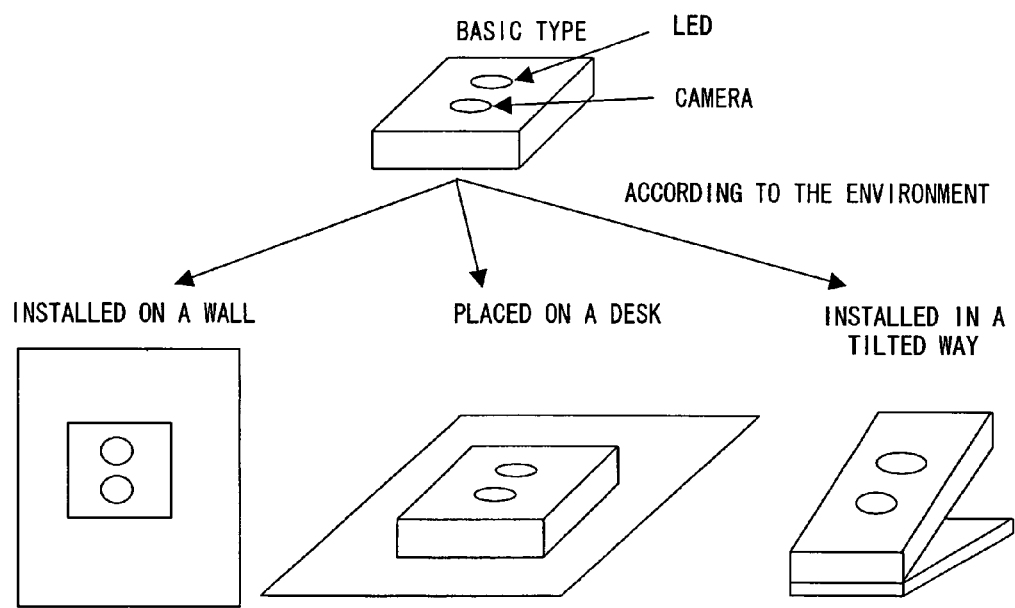
F I G. 7

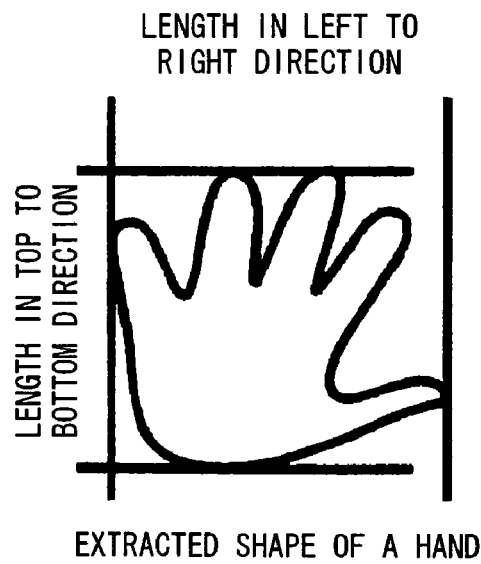 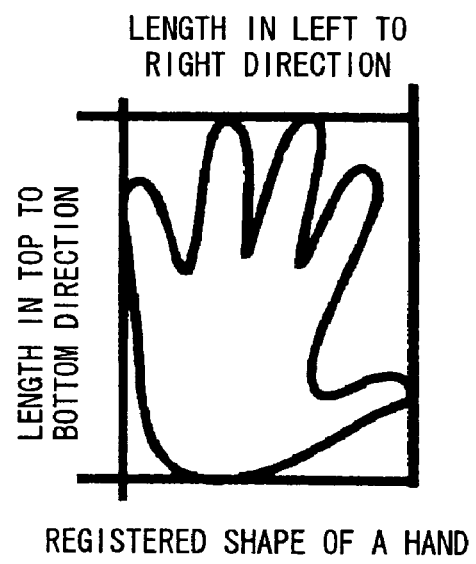
EXTRACTED SHAPE OF A HAND    REGISTERED SHAPE OF A HAND
F I G. 16

CARD READING DEVICE
INDIVIDUAL
IDENTIFICATION DEVICE
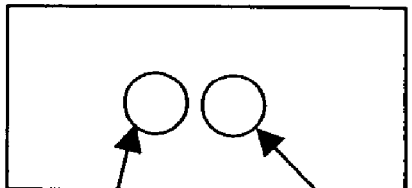
LED    CAMERA
F I G. 1 8

INDIVIDUAL IDENTIFICATION DEVICE

CROSS REFERENCE TO RELATED APPLICATION

This is a continuation of an International Application No. PCT/JP02/08944, which was filed on Sep. 3, 2002.

BACKGROUND OF THE INVENTION

1. Field of the Invention

The present invention relates to an individual identification device which identifies an individual not only by detecting an individual identification number (ID), but also by detecting bodily characteristics of an individual, more specifically, an image of blood vessels of a hand of the individual.

2. Description of the Related Art

As the method of confirming the identity of a person who, for example, enters and leaves a facility without assistance from anyone, there is a method which uses a magnetic card and a PIN (personal identification number). In these methods, however, there is a problem in that, for example, the magnetic card may be lost (forgotten) or plagiarized. As the method of confirming the identity of the person without having any risk of losing (forgetting) or plagiarizing the magnetic card, the method which uses bodily characteristics such as fingerprint and face has been studied.

The verification process of judging whether the user of the card is the individual who is represented by the card or the identification number, and the identification process of judging that the user is one of the specific people who have been registered are carried out according to the difference of bodily characteristics. The verification process and identification process are collectively referred to as individual identification.

Fingerprints, iris, face, blood vessels of a hand, etc. are used as bodily characteristics in individual identification. Instruments for measuring these characteristics are largely classified into a contact type and a noncontact type according to the measurement method. Since the individual identification of an unspecified large number of people needs to be implemented, for example, for the management of people who enter and leave a facility, a noncontact type instrument is more preferable in consideration of the sanitary aspect and psychological resistance of the user.

The bodily characteristic which is best used at present is a fingerprint, but as a finger must be pressed, the measuring instrument is a contact type instrument. As the instrument for measuring the iris, a noncontact type as well as a contact type is available, but there is a problem in that the instrument is expensive and the psychological burden of the user when the iris is imaged is large. The measurement of a user's face can be implemented using an inexpensive noncontact type camera, but it is not possible to make the identification accuracy very high due to the changes of countenance, etc.

The individual identification technology using a hand blood-vessel image was basically disclosed in patent document 1 and patent document 2 described below. Talking of the imaging of blood-vessels of a hand, there is a feature in that the user's psychological burden is small, and the identification accuracy is comparatively high, and that since the hand is imaged with near infrared radiation, the imaging of blood-vessels of a hand is strong against the changes of external light.

Patent document 1: British patent No. 2,156,127
Patent document 2: U.S. Pat. No. 4,699,149

Blood vessels of a hand can be imaged without bringing a hand into contact with the imaging device, but from the viewpoint of improving the identification accuracy, imaging a hand while having the hand fixed on the imaging device is more advantageous. Representative imaging devices commercially available at present are all contact type devices, which image the blood vessels of a user's hand which is brought into contact with part of the imaging device. Disclosed, for example, in patent document 3 below is an invention related to the product made by a Korean manufacturer which images the blood vessels of a hand, the back of which is pressed on the camera thereof. This product is of the type which images the back of one's hand while one holds a pole with one's hand. Disclosed in patent documents 4 and 5 are the inventions related to a product made by a U.S. manufacturer which images the palm of one's hand while one holds a pole with one's hand.

Patent document 3: Kokai (Japan. unexamined patent publication) No. H10-295674
Patent document 4: Kokai No. H11-512203
Patent document 5: U.S. Pat. No. 5,793,881

The individual identification devices using an image of blood-vessels of a hand which are commercially available at present are of the contact type in which a hand must be pressed on the devices, and these contact type devices have a problem in that from the viewpoint of a sanitary aspect and a feeling of cleanliness, the psychological burden of a user is large, and the devices become sticky particularly in summer, so that imaging blood vessels of a hand in a noncontact way is preferable. However, there is a problem in that when blood vessels of a hand are imaged in a noncontact way, it is difficult to obtain good blood-vessel images.

A first problem pertaining to the imaging of blood vessels in a noncontact way is that since blood vessels are imaged without fixing a hand, the opening, position and direction of the hand change each time the blood vessels of the hand are imaged. A second problem is that since, for example, near infrared radiation does not sufficiently cover the blood vessels of the hand, this imaging method is easily affected by external light.

In order to produce a better image of blood vessels, it is preferable to irradiate the surface of the hand skin almost orthogonally with near infrared radiation and also to make the optical axis of the camera orthogonal to the surface of the hand skin. However, there is a third problem in that when blood vessels of a hand are imaged in a noncontact way, the hand, camera and near infrared radiation are not necessarily arrayed in an optimum position, so that the quality of the image is prone to deteriorate.

In view of the above-described problems, the present invention has been developed to realize an individual identification device in which the psychological burden of a user is small and which is sanitary and cleanly by imaging blood vessels of a hand without bringing the hand into contact with the imaging device. It is difficult to obtain a good image of blood vessels under a noncontact condition, but it is the purpose of the present invention to make it possible to obtain a good image of blood vessels under a noncontact condition by contriving the configuration of the imaging device and to realize sufficient identification accuracy by using an identification method suitable for imaging blood vessels in a noncontact way.

SUMMARY OF THE INVENTION

In order to image blood vessels of a hand in a noncontact way, the individual identification device of the present invention uses an imaging device which comprises a position/direction/shape instructing unit for instructing the user to hold up his hand, one or more irradiating units for irradiating the hand with near infrared radiation, and one or more imaging units for producing an image by the near infrared radiation, and which can image blood vessels of a hand without coming into contact with the hand. The individual identification device also comprises a blood-vessel image extraction unit for extracting the blood-vessel image from the produced image, a blood-vessel image storage unit for storing the registered hand blood-vessel image of each user, and an identification unit for identifying a user by comparing the extracted blood-vessel image with the registered blood-vessel image.

As the position/direction/shape instructing unit, a unit in which the plane toward which the user holds up his hand is flat and which indicates the proper position and direction of the hand by means of a figure is used.

Furthermore, the individual identification device of the present invention comprises a hand position and/or direction detection unit for detecting the position and/or direction of a hand each time a blood-vessel image is extracted, and a correction unit for correcting the extracted blood-vessel image and giving the corrected image to the identification unit when the correction result is appropriate, and when the correction result is inappropriate, the position/direction/shape instructing unit notifies the user to that effect.

BRIEF DESCRIPTION OF THE DRAWINGS

FIG. 2 is a block diagram showing the configuration of the individual identification device of the present invention.

FIG. 5 shows an example of a blood-vessel image.

FIG. 6 shows an example of the storage contents of the storage unit.

FIG. 7 shows the external appearance of the imaging device.

FIG. 16 shows the comparison of the shape of a hand on an image with the registered shape of a hand.

FIG. 18 shows a combination of an individual identification device with a contact type card-reading device.

DESCRIPTION OF THE PREFERRED EMBODIMENTS

Figure 1:
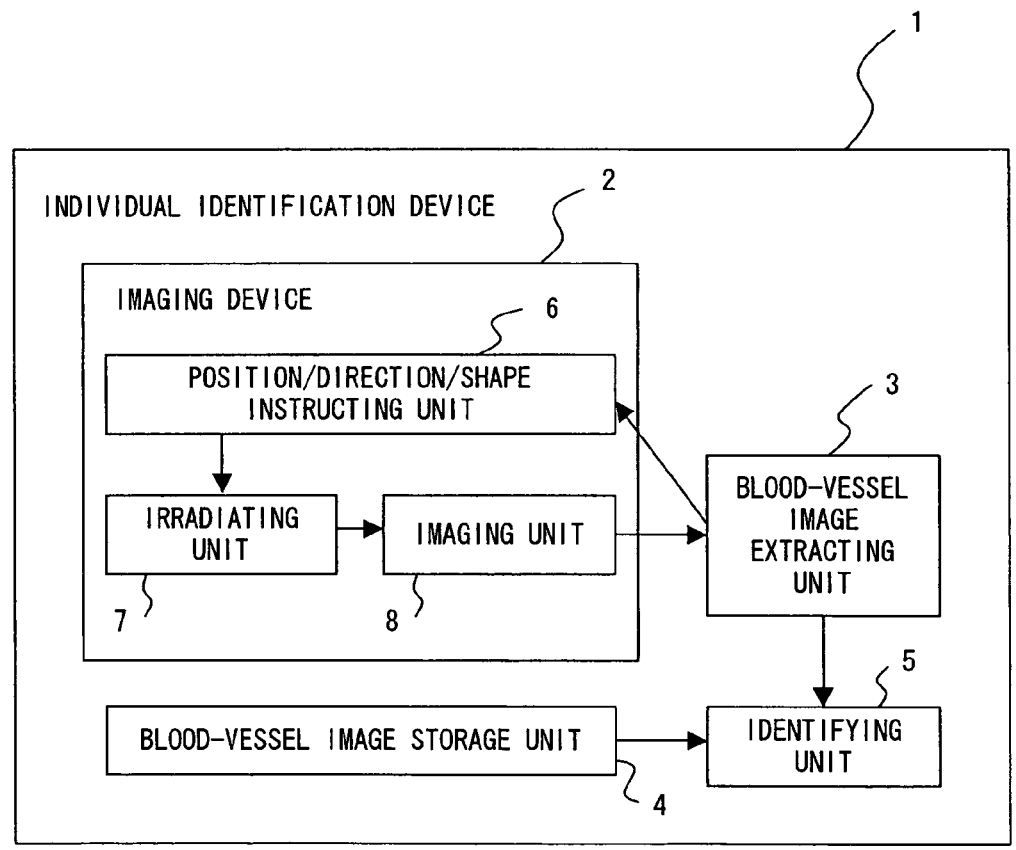
FIG. 1 is a block diagram showing the configuration of the principle of the present invention.

FIG. 1 is a block diagram showing the configuration of the principle of the individual identification device of the present invention. FIG. 1 shows the principle of a device which detects a hand blood-vessel image and identifies an individual, and the individual identification device 1 comprises an imaging device 2, a blood-vessel image extraction unit 3, a blood-vessel image storage unit 4, and an identification unit 5.

The imaging device 2 comprises a position/direction/shape instructing unit 6 for instructing a user to hold up his hand, one or more irradiating units 7 for irradiating the hand with near infrared radiation, and one or more imaging units 8 for producing an image by the near infrared radiation, and images blood vessels of a hand without coming into contact with the hand.

The blood-vessel image extraction unit 3 extracts the blood-vessel image from the image produced by one or more imaging units 8, the blood-vessel image storage unit 4 stores the registered hand blood-vessel image of each user, and the identification unit 5 identifies the user by comparing the extracted blood-vessel image with the registered blood-vessel image.

In an embodiment of the present invention, as the position/direction/shape instructing unit 6, a unit in which the plane toward which the user holds up his hand is flat and which can indicate the proper position and direction of the hand by means of a figure is used. As an example of the figure, a hand print can be used. It is possible to install a transparent plate or a half mirror toward which the user holds up his hand in front of the camera, and to house the imaging device in a hole of or along the groove provided in the identification device.

A variety of technologies are used to improve the practicability and identification accuracy of the individual identification device. For example, a plate which makes near infrared radiation transmit on the plane toward which the user holds up his hand is used to reinforce the intensity of the imaging device, and a mounting stand which can adjust the plane toward which the user holds up his hand to any arbitrary angle is used.

According to an embodiment of the present invention, the imaging device comprises a plurality of irradiating units 7, and a plurality of irradiating units can control the radiation of near infrared light according to the coming of external light other than near infrared light into one or more imaging units 8. Next, to improve the identification accuracy, the individual identification device 1 can comprise an detection unit for detecting the position and/or direction of a hand from the hand image produced each time a blood-vessel image is extracted and a correction unit for correcting the extracted blood-vessel image and giving the corrected image to the identification unit 5 when the correction is appropriate according to the detected position and/or direction of a hand. When the correction is inappropriate, the position/direction/shape instructing unit 6 can notify the user to that effect.

In this case, the detection unit can detect the direction of the hand according to the non-uniformity of the intensity of reflected light on the image, and the position and/or direction of the hand according to the shape of the hand on the image. Furthermore, the individual identification device 1 can comprise a hand-shape storage unit for storing the parameter of each user which is registered according to the shape of the hand, and the detection unit compares the registered parameter with the parameter on the image and can obtain the direction of the hand.

The detection unit approximates the hand on a plane and detects the direction of the hand, and the correction unit can correct the blood-vessel image using the parameter representing the plane.

According to an embodiment, the individual identification device 1 can comprise a unit for judging whether a hand is held up over the imaging device 2, an identification control unit for making the identification unit 5 identify an individual when the hand is judged to be held up over the imaging device 2.

Furthermore, the individual identification device 1 can comprise not only a plurality of imaging units 8, but also a calculation unit for calculating a three-dimensional shape of hand from the hand images produced by a plurality of imaging units 8 and a correction unit for correcting the extracted blood-vessel image according to the calculation result.

Next, the individual identification device of the present invention comprises the imaging device 2 which comprises one or more irradiating units 7 and one or more imaging units 8 and which, being compact, portable and pen-shaped, can image blood vessels of a hand without coming into contact with the hand, the blood-vessel image extraction unit 3, the blood-vessel image storage unit 4, and the identification unit 5.

In this case, the individual identification device 1 can further comprise a joint mechanism which enables the imaging device 2 to be rotated, a photographic tripod for fixing the imaging device, and a mounting unit for mounting the imaging device on the external connecting mechanism of a computer.

According to the present invention, it is possible to image blood vessels of a hand in a noncontact way, detect the position and direction of the hand as the occasion arises, and correct the position and direction of the hand if the position and direction of the hand are inappropriate in order to improve the identification accuracy.

Figure 3:
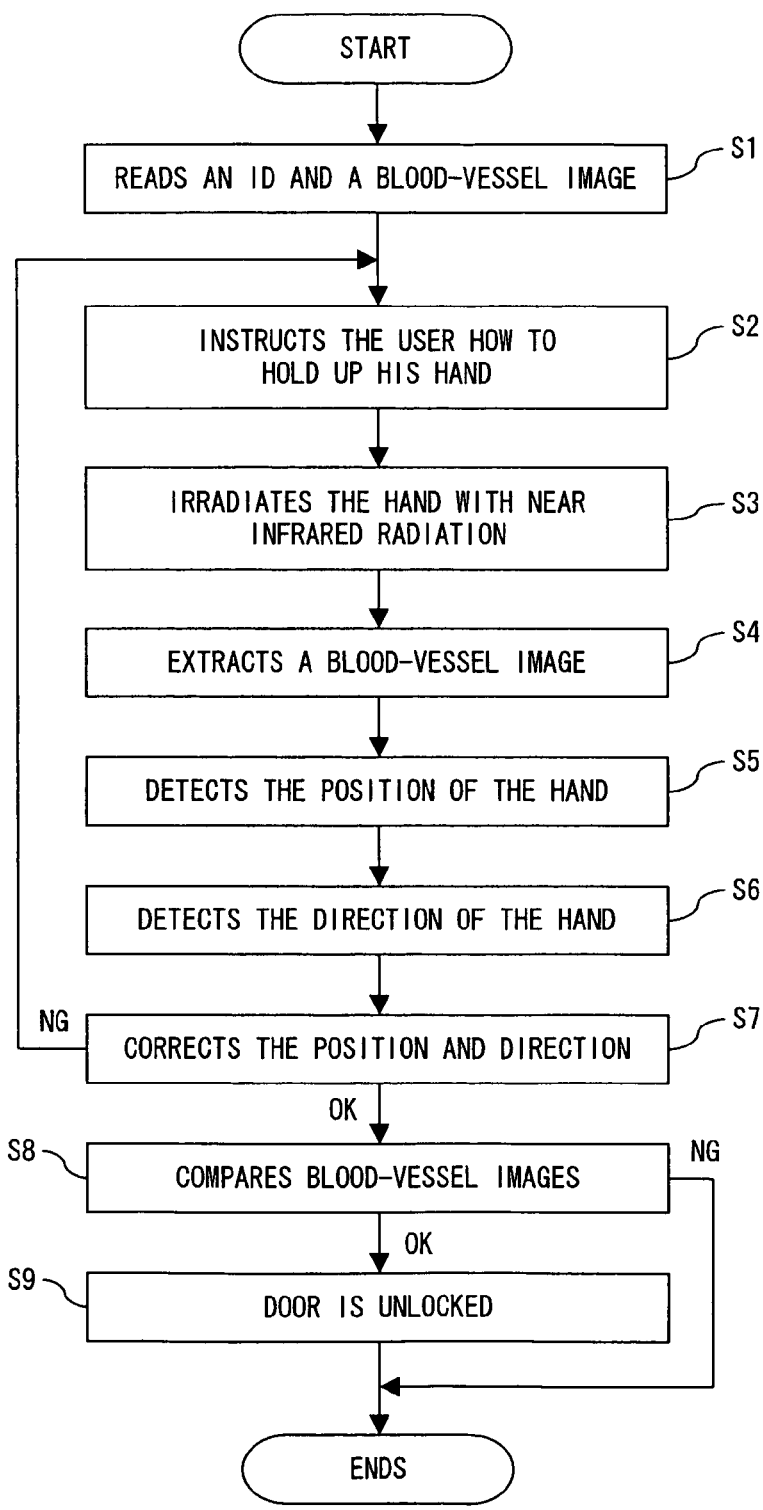
FIG. 3 is a flowchart showing the processing of individual identification.

FIG. 2 is a block diagram showing the individual identification device in the embodiment of the present invention, and FIG. 3 is a flowchart showing the processes of identifying an individual. The individual identification device irradiates some parts of a human body, the blood vessels of which can be easily imaged, such as the palm of a hand, the back of a hand, and a wrist, with near infrared radiation, images the intensity distribution of the reflected or transmitted light, and extracts a blood-vessel image from the image. Generally, individual identification is performed based on the judgement of whether the blood-vessel image which has been imaged with the individual identification device conforms to the blood-vessel image stored in the individual identification device, and the outcome is outputted.

In FIG. 2, the irradiating unit 10 is, for example, an LED (light emitting diode) which emits near infrared radiation, and a number of LEDs can be used as the occasion arises. The imaging unit 11 is a CCD camera or a CMOS camera, and a plurality of cameras can be used as the occasion arises.

The position detection unit 12 and the direction detection unit 13 are the units for detecting the position and direction of a hand from the produced image, and the position and direction correction unit 14 corrects the position and direction of the blood-vessel image based on these detection results to improve the identification accuracy. However, if the correction amount is larger than a prescribed value, the position and direction correction unit 14 judges that the correction is inappropriate, and does not conduct any correction. In that case, the position/direction/shape instructing unit 15 notifies the user that the correction is inappropriate.

In FIG. 2, the registered blood-vessel image of each individual is stored in the form of, for example, a card 16, and the ID and blood-vessel image data of each individual e.g. data corresponding to each pixel of a blood-vessel image are stored in the card 16, and the data are read by a card reading unit 17, and then are given to the identification unit 18. Here, a card is supposed to be used as a storage unit 16, but an external storage device such as a hard disk can be also used.

The position detection unit 12, direction detection unit 13, position and direction correction unit 14, card reading unit 17, and identification unit 18 are generally realized as a computer and a program thereof, but all these units do not necessarily need to be housed in the same computer. For example, the identification unit 18 can be realized by a host computer connected by a network as a matter of course.

In FIG. 2, the individual identification device combined with an automatic door is supposed to be applied to the control for entering a room. When someone is identified to be an individual who conforms to the individual ID of the card by the identification unit 18, the door is unlocked by a control unit 19, and the individual can enter the room.

When the processing starts in the identification processing shown in FIG. 3, first, the ID of the card which is inserted into, for example, the card reading unit and the registered blood-vessel image corresponding to the ID are read in Step S1. In Step S2, how to hold up a hand is instructed. Details of this instruction will be described later. In Step S3, near infrared radiation is radiated, and in Step S4, a blood-vessel image is extracted from an image produced. Details of this extraction will be described later.

Since, generally, an image of the whole hand is included in the produced image, the position of the hand is detected using the produced image in Step S5, and the direction of the hand is detected using the produced image in Step S6, and the position and direction of the extracted blood-vessel image is corrected using these detection results in Step S7 so that the identification accuracy is improved. Details of the detection and correction will be described later. When the correction is inappropriate, how to hold up a hand is instructed again in Step S2.

In Step S8, the blood-vessel image which has been extracted and corrected is compared with the registered blood-vessel image read in Step S1, and if the former conforms to the latter, the door is unlocked in Step S9, and if the former does not conform to the latter, the door is not unlocked, and the processing ends.

The individual identification processing is classified into the verification process of identifying a specific individual corresponding to the ID and the identification process of judging that the individual is a specific person among a plurality of users. Details of these processes will be described later. The processing procedure of the verification process is as follows.

1. Input of ID: An individual ID designated by a card or an identification number is received. However, when the verification processing is repeatedly performed for the individual ID of the same person, the input of the ID can be omitted.

2. Acquisition of a registered blood-vessel image: A registered blood-vessel image designated by an inputted individual ID is acquired from the storage unit 16. When the verification processing is repeatedly performed, the registered blood-vessel image in the previous verification processing is kept stored and can be used as it is.

3. Acquisition of a blood-vessel image produced: A blood-vessel image produced is acquired from the imaging unit 11.

4. Calculation of the degree of similarity: The degree of similarity indicating the extent of conformity of the two images is calculated.

5. Judgement: If the degree of similarity is larger than a prescribed threshold, the verification processing is successful, and the user is judged to be the individual represented by the individual ID. Unless the degree of similarity is larger than a prescribed threshold, the verification processing is unsuccessful, and the user is judged to be another individual.

On the other hand, the processing procedure of the identification unit 18 which performs the processes of identification is as follows.

1. Acquisition of a registered blood-vessel image: Blood-vessel images of a plurality of persons registered in the storage unit 16 are acquired. When identification processing is repeatedly performed, the registered blood-vessel images in the previous verification processing are kept stored and can be used as they are.

2. Acquisition of a blood-vessel image produced: A blood-vessel image produced is acquired from the imaging unit 11.

3. Calculation of the degree of similarity: The degree of similarity indicating the extent of conformity of the registered blood-vessel image and the produced blood-vessel image of each individual is calculated.

4. Judgement: An individual whose degree of similarity is the largest is selected. If the maximum value of the degree of similarity is smaller than a prescribed threshold, it is judged that there is no corresponding person (there is no corresponding person registered). Unless the maximum value of the degree of similarity is smaller than a prescribed threshold, the user is judged to be an individual whose degree of similarity is the largest.

Figure 4:
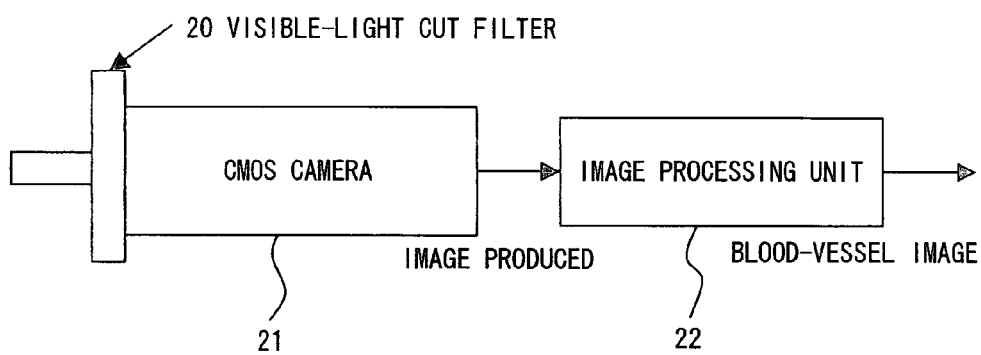
FIG. 4 shows an example of the configuration of the imaging unit.

FIG. 4 is an example of the configuration of the imaging unit 11 shown in FIG. 2. In FIG. 4, the imaging unit 11 comprises a visible-light cut filter 20 which intercepts visible light from input light, a CMOS camera 21, and an image processing unit 22 for extracting a blood-vessel image from the image produced by the CMOS camera 21.

It is preferable to use an LED which emits near infrared radiation as the irradiating unit 10 shown in FIG. 2. As the camera, a CCD camera can be used instead of the CMOS camera 21. A CMOS camera is compact and inexpensive, but a CCD camera can take a more beautiful image than a CMOS camera. Either of them can be selected according to their uses.

Since blood vessels are indicated by a dark pattern on the image produced, for example, by the CMOS camera 21 against the backdrop of an image of, for example, the whole hand, the blood vessels are extracted by performing binary processing to the image produced by the image processing unit 22. The binary processing is realized by setting the value of pixel to 1 when the (concentration) value of each pixel in an image is larger than a prescribed value and setting the value of pixel to 0 when the (concentration) value of each pixel in an image is not larger than a prescribed value. The binary processing can be also realized by a dedicated IC (microcomputer), or as a program within a computer as pre-processing by the identification unit 18 shown in FIG. 2. FIG. 5 is an example of the extracted blood-vessel image.

The degree of similarity which indicates the extent of the conformity of a produced blood-vessel image to a registered blood-vessel image is calculated, for example, as follows.

1. Initialization: The pixels to which one pays attention are set to the left top of an image. The variable (counter) holding the number of the pixels which conforms to the image is initialized to 0.

2. Comparison of pixel values: The pixel values of two images in the pixels to which one pays attention are acquired and compared. If the pixel values of the two images conform to each other, the value of the counter is increased by one.

3. Movement of the pixels to which one pays attention: The pixels to which one pays attention are moved to the left by one. If the pixels to which one pays attention exist at the right end, they are moved to the left end of one line below. If the pixels to which one pays attention exist at the right bottom, the movement of the pixels is terminated.

4. Repetition: The pixel values are compared again. (The processes in 2 and 3 above are repeated.)

5. Output of the similarity degree: The counter value is given as the degree of similarity.

The above method of calculating the degree of similarity has a problem in that the value of similarity degree is influenced by the position and direction in which a hand is placed. However, these influences can be decreased by improving the method of calculating the degree of similarity. In the above explanation, a binary image as it is used as a blood-vessel image, but in order to reduce the capacity of storage or increase the speed of identification processing, a method of calculating a characteristic quantity from the image and storing it, and calculating the degree of similarity by comparing the characteristic quantity when the identification device identifies a user can be also considered. As the characteristic quantity, it can be considered that, for example, characteristic points such as branch points and endpoints are extracted from an image, and those positions are used. In this embodiment, no reference is made to the details of the form of indicating blood-vessel images and the method of comparing blood-vessel images.

The storage unit 16 stores an individual ID and a blood-vessel image in association with each other, and is typically realized within a computer as a database in the form of storing data shown in FIG. 6. The blood-vessel image is stored by converting the value of each pixel of the image and the position of each characteristic point into a string of numerals according to a specific rule.

The registration processing of blood-vessel images can be also performed by the same device. The processing procedure is as follows.

1. Input of ID: An individual ID designated by a card or an identification number is received. However, if an individual ID has already been established, the input of the ID can be omitted.

2. Acquisition of a blood-vessel image produced: A produced blood-vessel image is acquired from the imaging unit 11.

3. Registration of a blood-vessel image: An individual ID and a produced blood-vessel image are registered in the storage unit 16.

When individual identification is conducted by imaging blood vessels of a hand in a noncontact way, the quality of the image produced is prone to deteriorate due to the opening, position, and direction of the hand, the influence of external light, and the correlation of the hand, camera and illumination, as already described above, so that the degree of similarity to the registered blood-vessel image of a user is prone to decrease. When the threshold of similarity degree is lowered to prevent the user from being judged to be another person, the probability that another person is judged to be the user increases on the contrary, and the identification accuracy lowers.

In this embodiment, to avoid the lowering of the identification accuracy, the position/direction/shape instructing unit 15 for instructing the user how to hold his hand is provided. In addition, some consideration is added to the identification method. First, described below are the details of the position/direction/shape instructing unit 15.

The hand is the organ which can be most freely moved in a human body, so it is possible to restrain the fluctuations which occur in holding up the hand to a minimum if an appropriate instruction is given to the user. Concretely speaking, the irradiating unit 10 (LED, etc.) and the camera are stored in a thin and flat imaging device so that the user naturally and unconsciously spreads the palm of his hand. Thus, the direction of the illumination and the optical axis of the camera can be made almost orthogonal to each other, and the quality of the image produced is improved. Moreover, there is another effect in that the opening of the hand can be stabilized.

To prevent the position and direction of the hand from fluctuating each time blood vessels are imaged, the appropriate position and direction of the hand on the plane on which the user should hold up his hand is indicated by a figure. As an example of the figure, a hand print can be used. Or, the tip position of a finger can be indicated by a point. The hand print is configured of a flat seal, or is made a three-dimensional shape using a material such as plastics. In the environment where the individual identification device is used by infants, to lessen the psychological resistance of infants, it can be considered that the imaging device is made, for example, as the shape of a life-size hand of a popular doll, and the infants are made to shake hands with that hand to perform individual identification.

When the correction processing which will be described later is judged to be inappropriate, an appropriate position and direction of a hand can be instructed to the user. For example, it is possible to mount an LED on the tip position of a finger and make the LED blink the positions in which the correction was inappropriate, or to array LEDs in a line to indicate an appropriate direction of the hand by means of a flow of light. In addition, it is possible to notify the inappropriate correction to the user by means of a phonetic sound, bell, lamp, etc. As the contents of the notification, merely a message stating that the correction is inappropriate, or the reason why the correction is inappropriate, for example, the direction is tilted, is notified.

It is preferable to make the imaging device have sufficient strength in consideration of the possibility that the imaging device may be hit by the palm of a hand. One method which makes the imaging device have the sufficient strength is to stick a transparent material such as plastics (for near infrared radiation) on the plane of the side of imaging blood vessels of a hand. At that time, if an opaque material is used for visible light, the internal structure is intercepted, and this can be a measure for preventing crimes. The imaging device is made to be as large in size as to be easily carried and mounted so that it can be mounted at a place where the user can easily hold up his hand according to the environment where blood vessels of the hand are imaged. A mounting stand is made mountable on the imaging device so that the imaging device can be mounted leaning over to one side. The external appearance of the imaging device is shown in FIG. 7.

Figure 8:
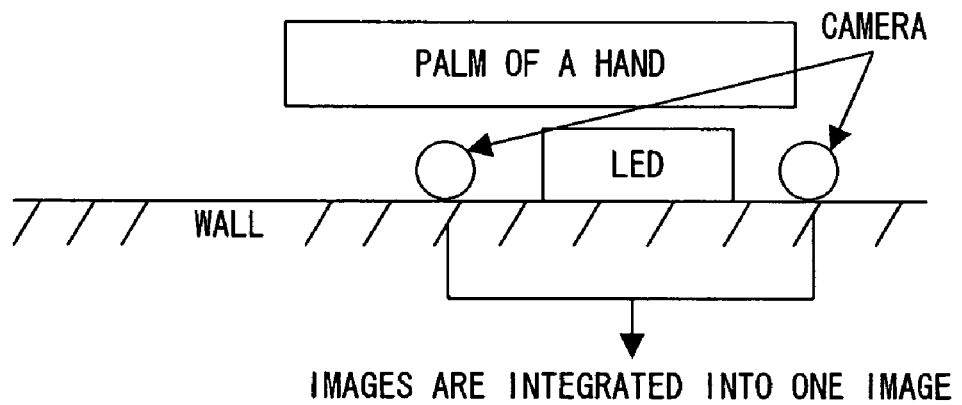
FIG. 8 shows the imaging method using a plurality of cameras.
Figure 9:
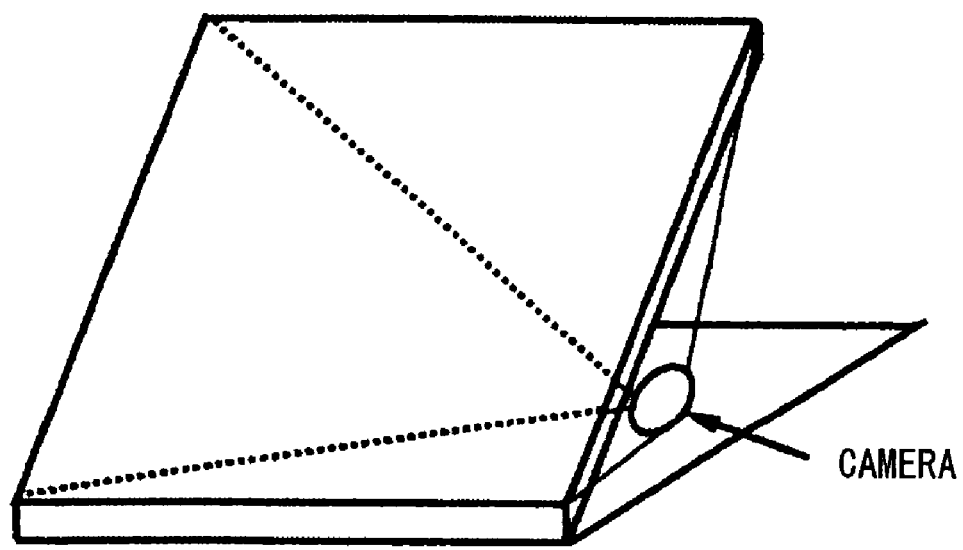
FIG. 9 shows an example of installing a transparent plate or a half mirror in front of the camera.

When the camera is very close to the hand, the scope of the hand to be imaged is so much limited that there is a possibility that the registered positions may not be imaged. As a method for solving this problem, there are a method of using a wide-angle lens like a fisheye lens and a method of arranging a plurality of cameras (FIG. 8). Images produced by a plurality of cameras are integrated into one image, and one image integrated is used for individual identification. Furthermore, there is a method of making the distance between the camera and the hand longer while making the user spread the palm of his hand by installing a transparent plate or a half mirror in front of the camera (FIG. 9).

Figure 10:
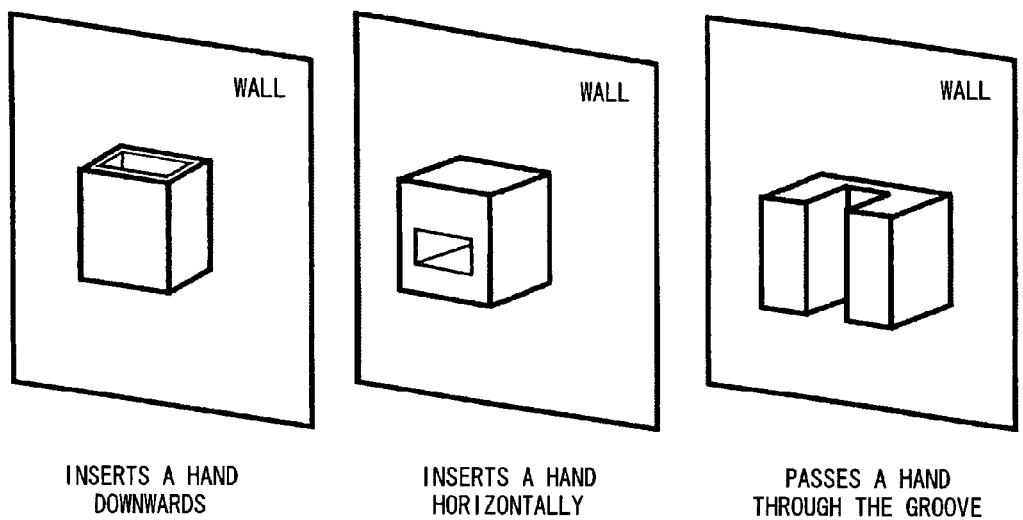
FIG. 10 shows the way how to insert a hand to get rid of the influence of external light.
Figure 11:
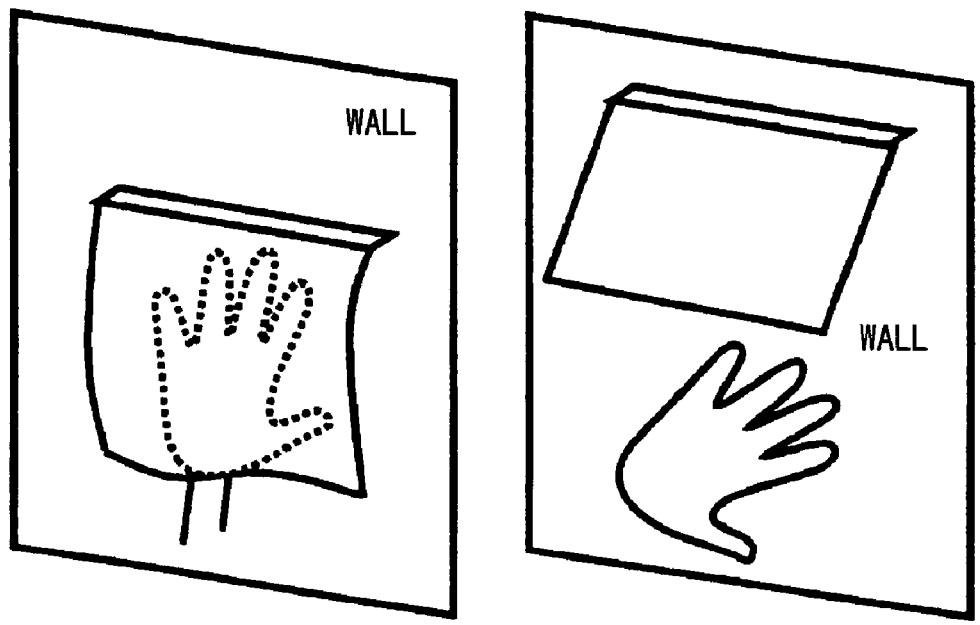
FIG. 11 shows the use of a split curtain or a reflective plate to get rid of the influence of external light.

Since blood vessels of a hand are imaged by irradiating the hand with near infrared radiation, the imaging is not so much affected by external light. However, in the environment where plenty of external light comes in, such as outdoors, it is preferable to get rid of the external light as much as possible. As an example of the shape of the imaging device which removes external light, there are the following types of imaging devices shown in FIG. 7 which are housed in the hole or the groove (FIG. 10). In the left image shown in FIG. 10, the imaging device is mounted on the front and rear surfaces of the hole, and in the middle image shown in FIG. 10, the imaging device is mounted on the upper and bottom surfaces of the hole, so that the palm and back of a hand can be imaged at the same time. Also, there is such a type of imaging device in which a split-curtain type intercepting plate is placed behind the hand to be presented (left image shown in FIG. 11). It is possible to do without inserting the hand into the split curtain by installing a reflective plate inside of the split curtain (right image shown in FIG. 11). It is preferable to make the angle of the reflective plate variable.

Figure 12:
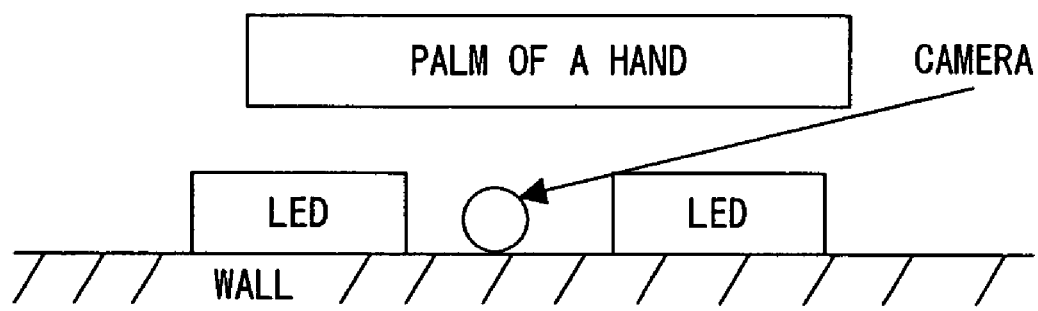
FIG. 12 shows the use of a plurality of illuminators to decrease the influence of external light.

As another means for decreasing the influence of external light, there is a method of raising the irradiating intensity of the illumination and irradiating the hand evenly by arranging a plurality of LEDs (FIG. 12). The illumination may be adjusted or switched so that the influence of external light is made small. For example, the direction of a sunray is calculated from the position in which the imaging device is installed and the present time, and the LED whose direction is similar to the direction of the sunray is lighted up.

Figure 13:
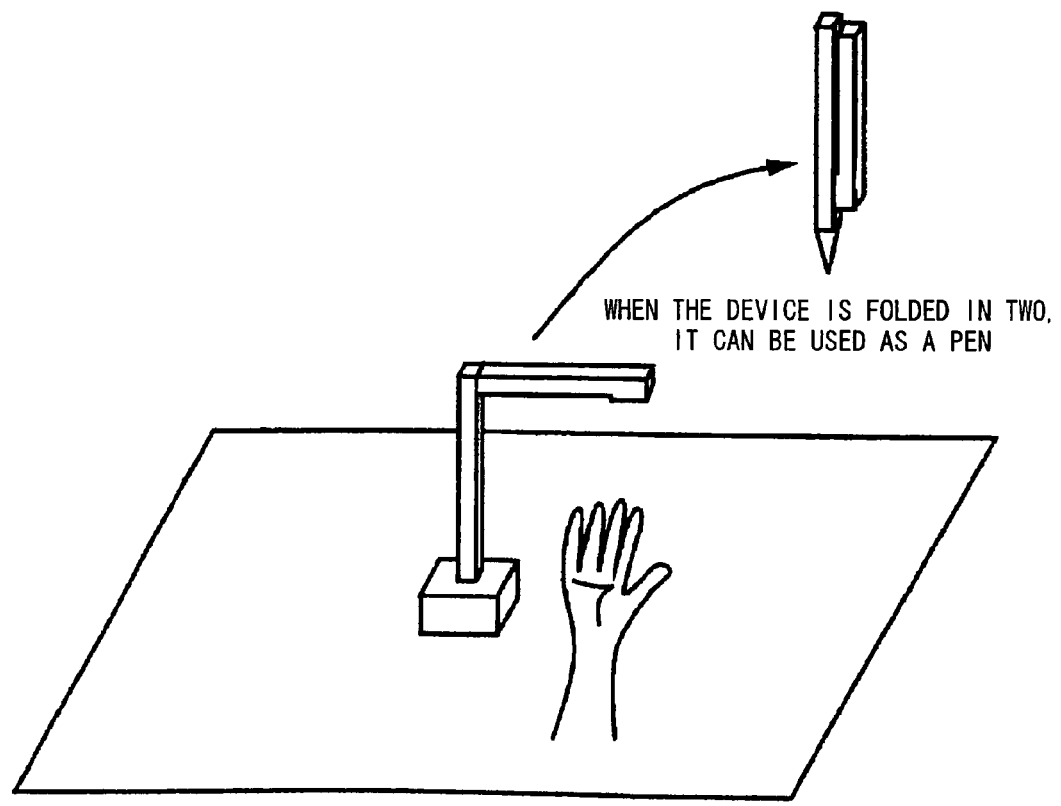
FIG. 13 shows an example of the shape of an easy-to-carry imaging device.

It can be also considered to get rid of the influence of external light by making the imaging device compact and easy-to-carry and installing such an imaging device in the place where no external light comes in when it is used. As the shape of the imaging device which realizes this method, there is a pen type device shown in FIG. 13. A camera and an LED are housed in the tip of the imaging device, and when the imaging device is used to image blood vessels of a hand, it is mounted on a fixing stand and its joint is bent. A fixing stand with holes in it and a tripod are used as tools for fixing the imaging device. When the imaging device is used with a notebook type portable computer, it is possible to install and fix the imaging device in the computer (to be caught with a clip or to be pressed to an expansion slot).

The problem in that the position and direction of a hand change each time blood vessels of the hand are imaged is solved by detecting the position and direction of the hand each time blood vessels of the hand are imaged and performing the following processing based on the detection.

Appropriate correction processing is performed by the position and direction correction unit 14.

If the correction is inappropriate, the position/direction/shape instructing unit 15 notifies the user that the correction is inappropriate, and has the user correct the inappropriate correction.

Figure 14:
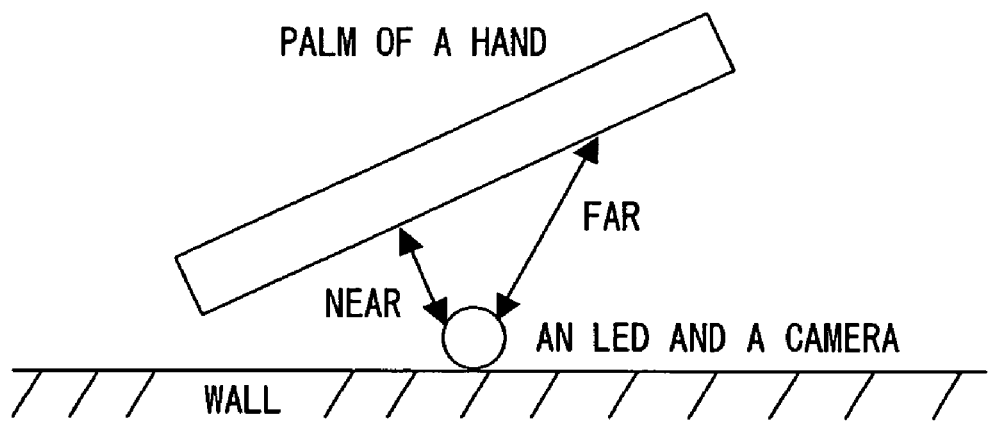
FIG. 14 shows the method of detecting the direction of a hand.

As the method of detecting the direction of a hand, there is a method of detecting the non-uniformity of, for example, reflective intensity. This method is based on the principle that when the palm of a hand is presented tilted to the camera, reflective intensity from remote places becomes smaller (FIG. 14).

The non-uniformity of reflective intensity is detected, for example, in the following manner. An image produced is divided into four parts, top, bottom, left and right, and the mean of the values of the pixels in each region (of each divided image) is calculated. If the difference of the four mean values calculated is small enough (to be judged according to whether the mean value is equivalent to or less than, for example, a threshold), the reflective intensity is judged to be uniform and the direction of the hand is judged to be flat. If not, the hand is judged to be tilted toward the direction in which the region in which the mean value is the highest becomes close to the hand.

Figure 15:
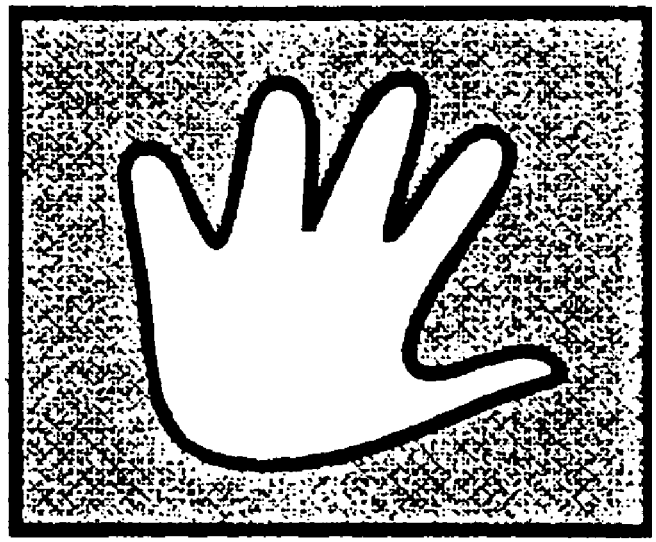
FIG. 15 shows the process of extracting the shape of a hand from an image.

As another method for detecting the direction of a hand, there is a method of obtaining the shape of a hand on an image. In this case, the visual field of a camera is widely set so that the whole of a hand can be imaged. The visual field of the camera may be expanded by a combination of a plurality of cameras. Since the hand is illuminated, the values of the pixels corresponding to the hand become large, and since the backdrop is not illuminated, the values of the pixels corresponding to the backdrop become small (FIG. 15). Thus, it is possible to obtain the shape of the hand on an image by extracting the pixels whose values are large by means of binary processing. The direction of the hand is obtained by comparing the extracted shape of hand and the registered (or mean) shape of hand. For example, the length of the hand in the top to bottom direction, and the length in the left to right direction are obtained from both the hand shapes, and the ratio between the two lengths (the ratio of the length in the top to bottom direction to the length in the left to right direction) is obtained. When the difference of this ratio is smaller than a prescribed threshold, the direction of the hand is judged to be flat. For example, the extracted shape of hand shown in FIG. 16 is short in the top to bottom direction, the shape of the hand is judged to be tilted. As another comparing criterion, the ratio of the perimeter of a hand to the width of, for example, one finger is considered. This is because the width of a finger is almost the same even when the hand is tilted.

Described below is the method of correcting the direction by the identification unit 18. The direction of a hand is corrected by combining images of a hand viewed from its front based on the detected tilt of the hand. For example, the palm of a hand is approximated on a plane, and the direction of the hand is obtained. The plane is indicated by three parameters a, b, and c (mean distance and tilt in top to bottom direction and in left to right direction) as in $z=ax+by+c$. When these parameters are assumed based on the above-described detection of non-uniformity, for example, the reflective intensity is supposed to be inversely proportional to the square of the distance as the relationship between reflective intensity and distance. Since the mean distance in each region of an image can be calculated based on this supposition, the following equation is obtained by the number of the regions.

Mean distance=$a$*value of coordinates in the left to right direction of the center of a region+$b$*value of coordinates in the top to bottom direction of the center of a region+$c$ Parameters a, b, and c are obtained by solving this equation. The use of these parameters makes it possible to combine the images of a hand viewed from its front by means of a projective transformation. The details are described in, for example, patent document 6.

Patent document 6: "Image Analysis Handbook" published by Tokyo University Shuppankai In the parameters obtained on the plane, a and b represent the tilt of the hand. These absolute values indicate the extent of the correction. If the extent of the correction is large, the image quality after the correction is made deteriorates and the identification accuracy lowers. Then, whether the correction is appropriate or inappropriate is judged depending on whether, for example, $|a|+|b|$ is larger than a given value. When the correction is judged to be inappropriate, that is notified to the user without performing any correction processing.

When the direction of a hand is corrected from the shape of the hand on an image as described above, either a method of obtaining the above-described parameters on the plane and conducting a projective transformation is used, or a method of expanding an image in the ratio of the length in the top to bottom direction to that in the left to right direction, which is an easier method than the former, is used. When characteristics extracted from the image are used as a blood-vessel image, the characteristics obtained from images photographed from the front of a hand may be directly combined without combining images photographed from the front of the hand.

Next, described below is the method of detecting the position of a hand. The position of a hand is detected by obtaining the shape of the hand on an image as described above. The visual field of the camera is widely set so that the whole of the hand can be imaged. The visual field of the camera may be expanded by a combination of a plurality of cameras. The shape of the hand can be obtained on an image by extracting the pixels whose values are large by binary processing as described in FIG. 15. The mean position of the pixels corresponding to the hand is determined as the mean position of the hand. By obtaining the mean position of the hand for registered data as well in advance, the discrepancy of both positions is corrected when identification is conducted. More specifically, the discrepancy of both positions is corrected by performing the parallel movement processing of the amount represented by the difference of both positions for the values of the pixels of the image photographed.

Finally, described below is the timing for performing identification processing. Usually, the time required for individual identification when one enters or leaves a building is not fixed, so basically, the imaging unit 11 must be operated at all times. However, when the action of card presentation, identification number input, etc. is done beforehand, it suffices to operate the imaging unit 11 for a specific time after then. Furthermore, the position/direction/shape instructing unit 15 may urge the user to hold up his hand. The imaging unit 11 repeats the processes of imaging blood vessels of a hand and extracting a blood-vessel image. From the viewpoint of preventing the malfunction of the process of extracting a blood-vessel image, it is preferable to judge whether a hand is held up and extract a blood-vessel image only when the hand is held up. Whether the hand is held up is judged by, for example, whether the mean value of the pixels of the image photographed is equivalent to or more than a threshold. It is also possible to select an optimum image from among a plurality of images which are successively photographed. As the selection criterion, for example, the image photographed, the mean value of the pixels of which is the largest is used, or the image photographed, the area of the shape of hand of which is the largest is used.

Described below is the method of further improving identification accuracy by taking advantage of the fact that the identification device can image blood vessels of a hand in a noncontact way.

1) Combined Use of the Shape of a Hand

Identification accuracy is improved by using the detection of the shape or direction of a hand and using them for identification. The shape of a hand is registered together when an ID and a blood-vessel image are registered, and the conformity of the shape of a hand is added as a material for judging when identification is conducted. The shape of a hand when being registered is freely determined by the user. For example, an image of blood vessels in the thumb joint which is photographed while a hand is clasped is registered. When identification is conducted, whether the hand is in a clasped state is judged from, for example, the ratio of the length of the shape of the hand in the top to bottom direction to the length in the left to right direction. Only when the degree of similarity of the blood-vessel image is equivalent to or more than a threshold and the hand is in a clasped state, the user is identified as such.

2) Identification of a Plurality of Parts of a Hand

Identification accuracy is improved by identifying a plurality of parts of a hand. A wide area of a hand is imaged by arranging a plurality of cameras. Particularly, in the imaging device whose hole a hand is inserted, both sides of the hand can be imaged as described above. As for the identification method, when one is judged to be the user in various positions of the wide area of the hand, one is judged to be the user, or one is the person whose sum of the degree of similarity is the largest.

When blood vessels of a hand are imaged successively, identification accuracy is improved by identifying a plurality of parts of a hand in order. Which part of a hand is being presented is judged from, for example, the shape of the hand on an image. Furthermore, the order of the presentation can be used for identification.

Further described below are other methods for improving identification accuracy.

1) Calculation of a Three-Dimensional Shape

Figure 17:
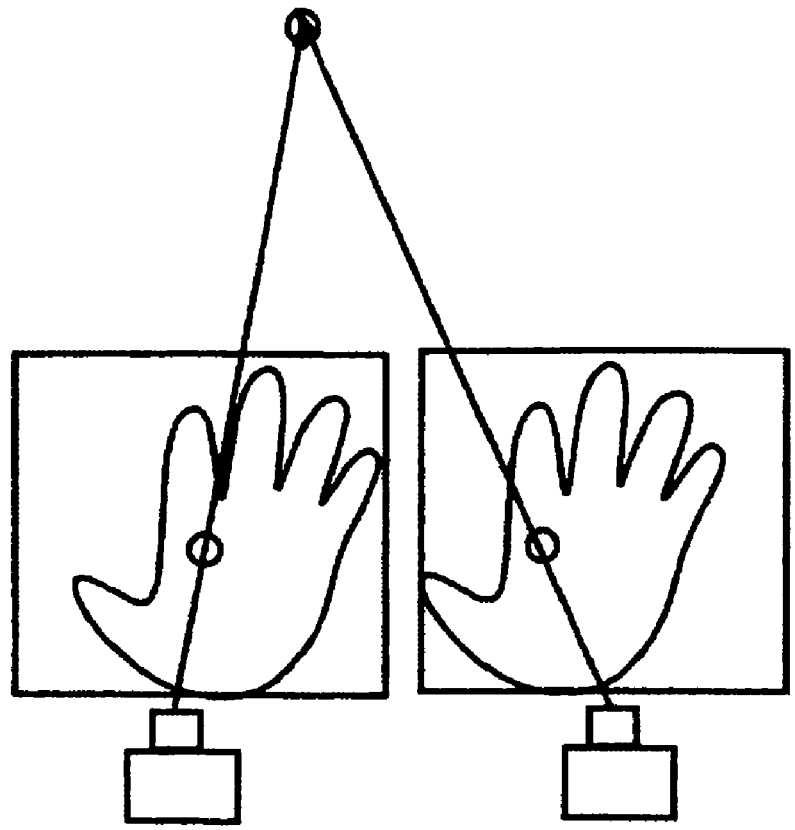
FIG. 17 shows the stereo measurement of the shape of a hand.

Described below is the technology which calculates a three-dimensional shape of a hand from a photographed image as the technology which makes identification with higher accuracy possible. Since the technology of calculating a three-dimensional shape of a substance from an image is a publicly known art, the details of said technology are omitted. For example, refer to patent document 6. A three-dimensional shape of a hand is obtained by arranging a plurality of cameras and implementing stereo measurement. Stereo measurement is implemented by finding corresponding points in two images (FIG. 17).

The use of a calculated three-dimensional shape makes the process of correcting a photographed image even more accurate. The method of correcting a photographed image is the same as that described before. Furthermore, a three-dimensional shape of blood vessels is obtained by implementing stereo measurement for an extracted blood-vessel image. By calculating the degree of similarity three-dimensionally, identification with higher accuracy is made possible. A three-dimensional shape of blood vessels can be calculated from motion parallax using a plurality of successive images instead of a plurality of cameras. Moreover, a three-dimensional shape of blood vessels can be calculated by switching the illumination and making the illumination have a specific pattern.

2) Combined Use of Visible Light

When the palm of a hand is imaged, the wrinkles on the surface of the palm (lines on the palm) are also imaged. Since the wrinkles can be duplicated (stolen) comparatively easily, it is preferable not to use the wrinkles for individual identification. If imaging with visible light is used together, it is possible to separate wrinkles and blood vessels. Imaging with visible light is implemented, for example, by another camera. Or, the visible-light cut filter 20 shown in FIG. 4 may be partially removed. Since the wrinkles are imaged only with visible light, the wrinkles can be removed by removing the detection result obtained with visible radiation from the detection result obtained with infrared radiation. A blood-vessel image from which the wrinkles have been removed is registered and is compared with a photographed blood-vessel image from which the wrinkles have been removed. Or, the amount of the wrinkles which have been removed is calculated, and when there are plenty of wrinkles, the user is given a warning to change the opening of his hand.

Next, described below is the method of improving users' convenience. In the individual identification for example, for the control of entering and leaving a room, first, a user presents his ID to the identification device by means of a card (an IC card, etc.), and then he holds up his hand to verify his ID. When a noncontact type IC card is used, there is no particular problem in operating the card, but when a contact type card or an insertion type card is used, the card is operated by hand, and after then the hand must be held up again, thus causing a problem in that the operation becomes complicated. Described hereinafter is the method of solving this problem.

1) Wrist or Back is Imaged while Holding Up a Card

When a card identification mechanism in which the surface of a card is touched to a card reading device is used, a camera of an individual identification device is installed under the card reading device to image a wrist (FIG. 18). Or, a camera is installed next to the card reading device, and after the process of reading a card finishes, the back of a hand is imaged while rotating the hand. Thus, individual identification is made possible by one-time operation.

2) Palm is Imaged after a Card is Inserted

Figure 19:
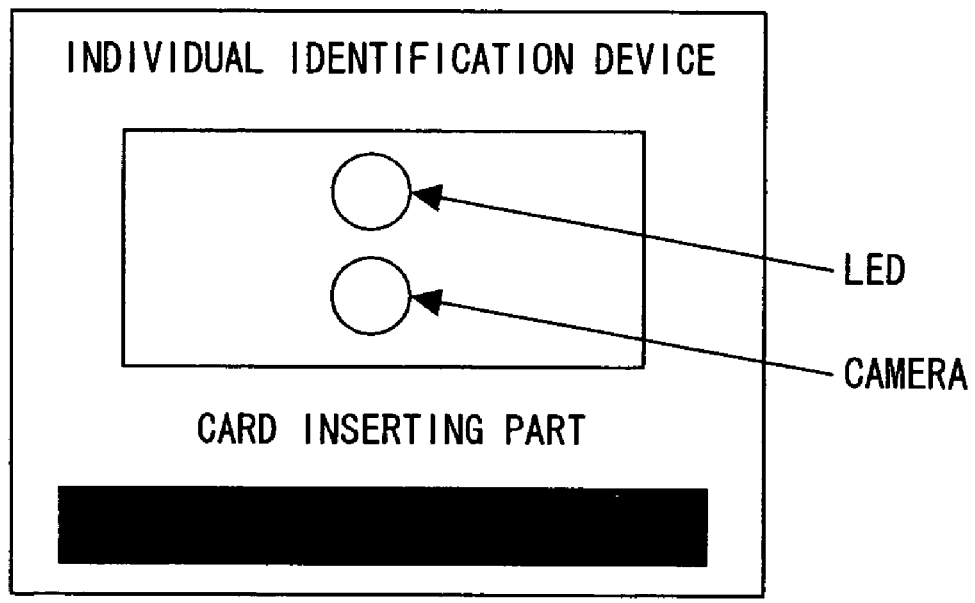
FIG. 19 shows a combination of an individual identification device with an insertion type card-reading device.

When a card identification mechanism in which a card is inserted into a card reading device is used, a camera of the individual identification device is installed on the card insertion part or above (in a higher position than) the card insertion part, and after a card is inserted, the palm of a hand is imaged (FIG. 19). The palm of a hand may be imaged while rotating the hand. Thus, individual identification is made possible by one-time operation. This method can be applied not only to the card identification mechanism in which a card is discharged from the insertion port but also to the card identification mechanism in which a user passes through a gate and receives his card at another place.

As another type of usage of an individual identification device, if the individual identification device is installed at the entrance of a conference room or a classroom to manage the attendance and absence of people at and from a conference or a class, the people are expected to rush to the device before a conference starts and some confusion is expected to occur. Described hereinafter is the method of solving this problem.

An individual identification device which stores blood-vessel images of all the attendants who are expected to attend a conference is circulated to one attendant after another during the conference, and individual identification is implemented successively. To enable each attendant to confirm that his attendance at the conference has been registered, it is preferable to include the identification unit 18 and an indication unit for indicating the result in the individual identification device to be circulated. As individual identification processing, verification processing is implemented after an individual ID is obtained by presenting a card, or identification processing without a card is implemented. Identification results are kept stored in the individual identification device, and after the individual identification device is finally collected, data is transferred to an attendance and absence management device and is calculated. When an encoding mechanism is built in the individual identification device, codes may be transmitted to the attendance and absence management device using a radio communications mechanism each time identification is conducted. The reason why data are encoded is because, for example, people who attend at an important secret meeting should not be made known.

Figure 20:
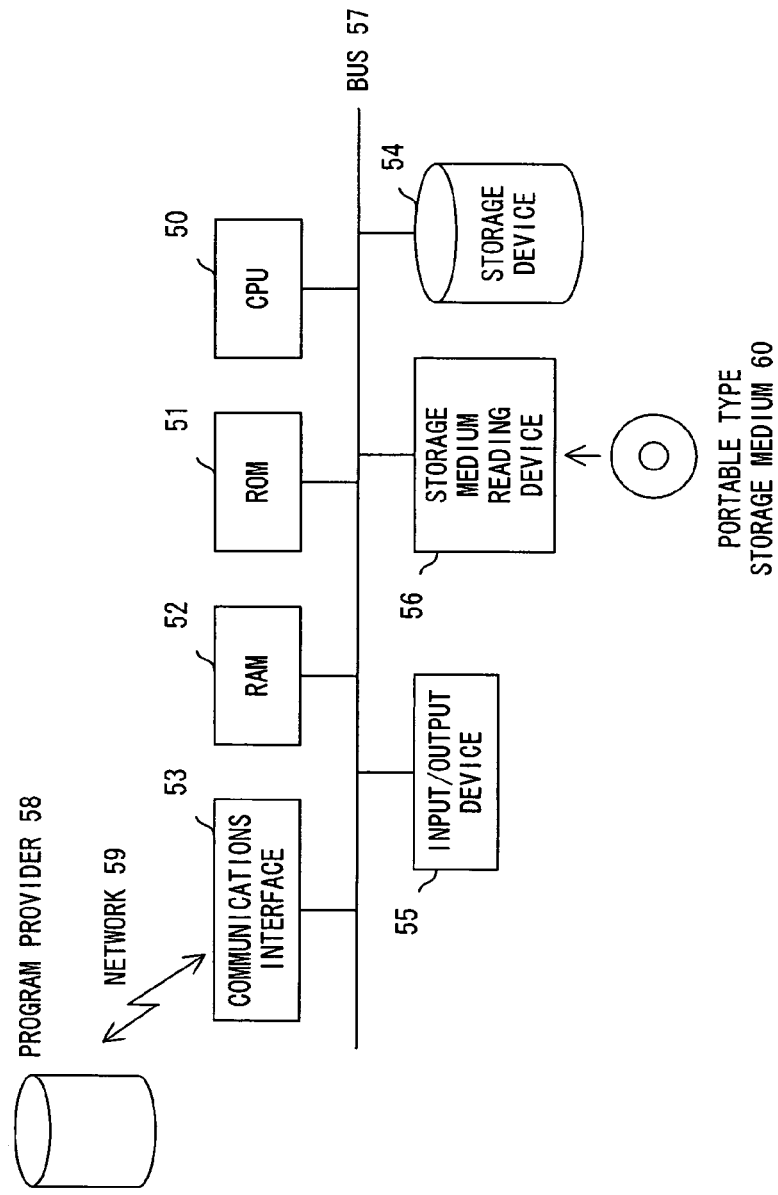
FIG. 20 shows the loading of a program onto a computer in the embodiment of the present invention.

Details of the individual identification device of the present invention have been explained so far. It is possible as a matter of course to configure this individual identification device as a computer system including an imaging device. FIG. 20 is a block diagram showing the configuration of such a computer system, i.e. the hardware environment.

In FIG. 20, the computer system comprises a central processing unit (CPU) 50, a read-only memory (ROM) 51, a random access memory (RAM) 52, a communications interface 53, a storage device 54, an input/output device 55, a portable-type storage medium reading device 56, and a bus 57 in which all these devices are connected.

As the storage device 54, various kinds of storage devices such as a hard disk and a magnetic disk can be used. A program shown in the flowchart of FIG. 3 and a program for detecting the position and direction of a hand, and for correcting blood-vessel images are stored in the storage device 54 or the ROM 51, and by executing the programs by the CPU 50, individual identification in the embodiment of using blood-vessel images photographed in a noncontact way is made possible.

These programs can be stored, for example, in the storage device 54 via a program provider 58, a network 59, and the communications interface 53, or can be stored in a portable-type storage medium 60 which is commercially sold and distributed, and set to the reading device 56, and executed by the CPU 50. As the portable-type storage medium 60, various types of storage media such as a CD-ROM, a flexible disk, an optical disk, and a magnet-optical disk can be used. By reading the programs stored in these storage media by the reading device 56, individual identification in the embodiment of using blood-vessel images is made possible.

According to the present invention, it is possible to provide an individual identification device in which the psychological burden of a user is small and which is sanitary and clean by imaging an image of blood vessels of a hand in a noncontact way, as already explained in detail. To avoid the drop of identification accuracy due to the imaging in a noncontact way, the form of identification device and the identification method are studied. For example, the position and direction of a hand are detected and a blood-vessel image is corrected according to the detection result, thus contributing a great deal to the improvement of the practicability of an individual identification device using an image of blood vessels of a hand.

The individual identification device of the present invention, which uses an image of blood vessels of a hand photographed in a noncontact way, can be used in all industries which require individual verification or individual identification, for example, for the management of people who enter and leave a facility or who attend a conference.

What is claimed is:

1. An individual identification device which uses an image of blood vessels of a hand to perform individual identification, comprising:
   an imaging device which can image blood vessels of a hand, comprising:
   a position/direction/shape instructing unit instructing a user to hold up his hand;
   one or more irradiating units irradiating the hand with near infrared radiation; and
   an imaging unit producing an image of the hand by the near infrared radiation responsive to reflection, by the hand, of the near infrared radiation irradiated by the one or more irradiating units; and
   a computer comprising:
      a processor;
      a storage device;
      the processor executes a process including:
         producing an image of the hand using the imaging device;
         extracting a blood-vessel image from the produced image of the hand;
         storing a registered hand blood-vessel image to the storage device;
         calculating a three-dimensional shape of the hand according to a position and/or direction of the hand from the produced image of the hand as a calculation result;
         correcting and outputting a corrected extracted blood-vessel image according to the calculation result when a correction not larger or equal to a specified amount is to be made and not outputting a corrected extracted blood-vessel image when a correction larger than the specified amount is to be made, and notifying the user of a correction result when the corrected extracted blood-vessel image is outputted; and
         identifying the user by comparing the extracted blood-vessel image with the registered blood-vessel image when the corrected extracted blood-vessel image is not outputted and by comparing the corrected extracted blood-vessel image with the registered blood-vessel image when the corrected extracted blood-vessel image is outputted.

2. The individual identification device according to claim 1, wherein the imaging device comprises a plate which makes near infrared radiation transmit on a plane toward which the user holds up his hand, the plate sticking on the imaging device to reinforce a strength of the imaging device.

3. The individual identification device according to claim 1, wherein the imaging device is mounted on a mounting stand which can adjust a plane toward which the user holds up his hand to any arbitrary angle.

4. The individual identification device according to claim 1, wherein the position/direction/shape instructing unit comprises a hand print placed on a plane sheet toward which the user holds up his hand.

5. The individual identification device according to claim 1, wherein
   the imaging device comprises a plurality of imaging units; and
   the blood-vessel image extraction unit extracts a blood-vessel image from a combined image of the images produced by the plurality of imaging units.

6. The individual identification device according to claim 1, wherein the position/direction/shape instructing unit comprises a transparent plate or a half mirror toward which the user holds up his hand which is installed in front of the imaging device.

7. The individual identification device according to claim 1, wherein the imaging device is housed in a hole of the individual identification device.

8. The individual identification device according to claim 1, wherein the imaging device is housed along a groove provided in the individual identification device.

9. The individual identification device according to claim 1, wherein the imaging device is equipped with a split-curtain shaped intercepting plate which intercepts external light from the imaging unit when the user holds up his hand.

10. The individual identification device according to claim 1, wherein
the process further including:
controlling the radiation of near infrared radiation by the irradiating units according to an incoming of external light other than near infrared radiation into the imaging unit.

11. The individual identification device according to claim 1, said position/direction/shape instructing unit further comprising a unit in which a plane toward which the user holds up the hand is flat and indicates a proper position and direction of the hand by means of a figure.

12. The individual identification device according to claim 1, wherein
the process further including:
detecting a position and/or direction of a hand from an image of the hand each time a blood-vessel image is extracted, and
correcting the extracted blood-vessel image according to the detected position and/or direction of the hand and giving the corrected image the computer when the corrected image is appropriate, and when the corrected image is in appropriate, making the position/direction/shape instructing unit notifies the user to that effect.

13. The individual identification device according to claim 1, wherein:
the process further including:
detecting the position and/or direction of a hand from the image of the hand each time a blood-vessel image is detected;
judging whether the detected position and/or direction of the hand is appropriate; and
notifying the user that the position and/or the direction of the hand is inappropriate when the position and/or the direction of the hand is inappropriate.

14. The individual identification device according to claim 1, wherein:
the process further including:
judging whether a hand is held up on a plane on which the user should hold up his hand; and
identifying an individual when the hand is judged to be held up on said plane.

15. The individual identification device according to claim 1, wherein the imaging device comprises a plurality of imaging units, and the plurality of imaging units image a plurality of parts of a hand at the same time.

16. The individual identification device according to claim 1, wherein the imaging unit images a plurality of parts of a hand in order.

17. The individual identification device according to claim 1, wherein the position/direction/shape instructing unit instructs the user to locate the hand at a variable distance from the imaging device.

18. The individual identification device according to claim 1, wherein the position/direction/shape instructing unit instructs the user to locate the hand at a variable position relative to the imaging device.

19. The individual identification device according to claim 1, wherein
the process further including:
correcting the extracted blood-vessel image responsive to radiation intensity; and
identifying the user by comparing the corrected extracted blood-vessel image with the registered blood-vessel image.

20. An individual identification device, wherein the device performs individual identification by detecting an image of blood vessels of a hand, comprising:
an imaging device which can image blood vessels of a hand in various positions including a distance and a direction of a palm of the hand in a noncontact way, and which has one or more irradiating units irradiating the hand with near infrared radiation, and imaging unit producing an image based on near infrared radiation reflected from the hand; and
a computer comprising:
a processor;
a storage device;
the processor executes a process including:
producing image of the hand using the imaging device;
extracting a blood-vessel image from the produced image;
storing a registered blood-vessel image to the storage device;
calculating a three-dimensional shape of the hand from the produced image of the hand according to a position and/or direction of the hand and producing a calculation result;
correcting a plane upon which the hand is assumed to lie and correcting the extracted blood vessel image according to the calculation result and outputting a corrected extracted blood-vessel image and notifying a user of the correcting when a correction result is not larger than a specified amount; and
comparing the registered blood-vessel image with the extracted blood-vessel image when the corrected extracted blood-vessel image is not outputted and comparing the registered blood-vessel image with the corrected extracted blood-vessel image when the corrected extracted blood-vessel image is outputted to perform individual identification.

21. A non-transitory computer readable portable type storage medium which is used by a computer which performs individual identification by detecting an image of blood vessels of a hand stores a program which directs the computer to execute:
instructing the user how to hold his hand;
receiving an image of the user's hand which includes a blood-vessel image produced by reflection of near infrared radiation from the hand;
extracting the user's hand blood-vessel image;
detecting the position and/or direction of the hand;
correcting the blood-vessel image according to the detected position and/or direction of the hand, outputting a corrected blood vessel image and notifying the user of the correcting and not correcting when a correction larger than a specified amount is to be made;
comparing a registered blood-vessel image with the corrected blood-vessel image when the corrected blood vessel image is output and comparing the registered blood-vessel image with the extracted user's hand blood-vessel image when the corrected blood vessel image is not output to perform individual identification.

22. An individual identification device which uses an image of blood vessels of a hand to perform individual identification, comprising:
an imaging device which can image blood vessels of a hand, comprising:
position/direction/shape instructing means for instructing a user to hold up his hand;

one or more irradiating means for irradiating the hand with near infrared radiation; and imaging means for producing an image by reflection of the near infrared radiation from the hand;

a computer comprising:

processor means;

storage means for storing;

the processor means for executing a process including:

producing image of the hand using the imaging device;

extracting a blood-vessel image from the produced image;

storing the registered hand blood-vessel image of each user to the storage means; and identifying the user by comparing the extracted blood-vessel image with the registered blood-vessel image.

23. An individual identification device, wherein the device performs individual identification by detecting an image of blood vessels of a hand, comprising:

a compact and portable pen shaped imaging device which can image blood vessels of a hand by holding the compact and portable pen type imaging device, and which has one or more irradiating units irradiating the hand with near infrared radiation, and one or more imaging units for producing an image based on reflection of near infrared radiation from the hand; and a computer comprising:

a processor;

a storage medium;

the processor executes a process including:

producing image of the hand using the imaging device;

extracting a blood-vessel image from the produced image of the hand;

storing a registered blood-vessel image of a user to the storage device;

calculating a three-dimensional shape of the hand from the produced image of the hand and the position and/or direction of the hand;

correcting a position of the hand based on a mean position of pixels of the hand according to the three-dimensional shape of the hand and outputting a corrected extracted blood-vessel image when a correction is not larger than a specified amount and not outputting when a correction is larger than the specified amount; and comparing the registered blood-vessel image with the extracted blood-vessel image when the corrected extracted blood-vessel image is not outputted and comparing the registered blood-vessel image with the corrected extracted blood-vessel image when the corrected extracted blood-vessel image is outputted to perform individual identification.

* * * * *